(12) United States Patent
Tse

(10) Patent No.: US 7,232,309 B2
(45) Date of Patent: Jun. 19, 2007

(54) ENDODONTIC PLATFORM AND USE THEREOF

(76) Inventor: James Tse, 12 Larkfield Drive, Toronto, ONT (CA) M3B 2H1

( * ) Notice: Subject to any disclaimer, the term of this patent is extended or adjusted under 35 U.S.C. 154(b) by 182 days.

(21) Appl. No.: 10/856,753

(22) Filed: Jun. 1, 2004

(65) Prior Publication Data

US 2005/0266374 A1    Dec. 1, 2005

(51) Int. Cl.
*A61C 19/04*    (2006.01)
(52) U.S. Cl. .......................................... 433/72; 433/49
(58) Field of Classification Search ............... 433/102, 433/224, 75, 72, 49, 77, 79, 25, 229, 163; 206/63.5, 368, 369
See application file for complete search history.

(56) References Cited

U.S. PATENT DOCUMENTS 3,358,826 A * 12/1967 Siegel .................... 206/368
4,028,810 A * 6/1977 Vice ....................... 433/75
4,353,694 A * 10/1982 Pelerin ..................... 433/77
5,265,724 A * 11/1993 Dondlinger ............... 206/366
5,289,919 A * 3/1994 Fischer .................... 206/571
6,036,490 A * 3/2000 Johnsen et al. ........... 433/102
6,464,497 B2 * 10/2002 Landoz .................... 433/77

* cited by examiner

*Primary Examiner*—Cris L. Rodriguez
*Assistant Examiner*—Patrick J. Kilkenny

(57) ABSTRACT

An platform for use with an instrument during an endodontic procedure. The platform includes a substantially rectangular-shaped body for holding the instrument pierced partly therethrough, a linear measure for establishing the working length of the instrument; and a reservoir for receiving a medicament. The platform may also include a removable marker for staking out distance along the linear measure and a plurality of scoreable stage markings for indicating the particular stage of the endodontic procedure.

19 Claims, 1 Drawing Sheet

ENDODONTIC PLATFORM AND USE THEREOF

TECHNICAL FIELD OF THE INVENTION

This invention is related to the field of endodontics, more specifically to a platform for use during an endodontic procedure with a rigid perforable body defining a medicament reservoir, and an instrument measure.

BACKGROUND OF THE INVENTION

During root canal therapy, an endodontic procedure, it is necessary for the professional (a dentist or endodontist) to use a number of instruments. In particular, instruments are employed by the dental professional to remove pulp tissues from the root canal once the pulp chamber is exposed.

Typically, such instruments, such as files, comprise a thin, flexible, metal shaft or file with an abrasive surface or sharp edges. A handle or hub end is attached on one end of the instrument and may be gripped by the dental professional or attached to a drill. Such instruments also include the bits of drills.

The instruments are inserted into a canal of the tooth during root canal therapy. In order to prevent penetration of such instruments beyond the canal apex, the file must be inserted no more than a specific distance inside the canal of the tooth. A determination must be made as to how far the file instrument can enter the canal prior to the insertion. Commonly, an adjustable stopper is placed over each file instrument along the shaft or file so that the distance between the tip of the instrument and the stopper is the same as the distance between the top surface of the tooth and the apex of the canal. Thus, the working length of the file is established.

During the root canal therapy, the application of medicament or a sterilizing solution to the file instrument is usually necessary. At all times, the hygiene of the entire system is of paramount concern. The ease with which used instruments may be collected for cleaning after a procedure without causing damage to the instruments and injury to the collector is also of concern.

U.S. Pat. No. 4,976,615 (Kravitz) is an example of an attempt to address some of the needs of the dental professional in the form of a platform adapted to be mounted on a dentist's finger. A foam insert holder mounted on the platform receives a removable foam insert for holding a plurality of root canal instruments. An open-ended slot formed in the platform is adapted to receive one of the instruments. Scale indicia is provided on the platform to permit adjustment of the working length of the file instrument in the slot to guide the dentist.

However, the platform in Kravitz is designed to receive a removable foam insert and hence to be re-usable; the other parts of the platform must be sterilized each time the platform is re-used; to dispose of the platform after each use is expensive. It also fails to provide means to hold medicament for the dental professional.

The platform disclosed in U.S. Pat. Nos. 5,368,482 and 6,036,490 (Johnsen et al.) includes a resiliently deformable cushion in a socket member. The cushion provides surface regions configured to receive endodontic instruments. The platform may be used to service the files. A finger mount is attached to the socket member. The platform may include a ruler. The description of a commercial version of this platform may be found at http://www.jordco.com.

This cushion of this platform is essentially rectangular in shape. This appears to be too narrow and offers insufficient space for a larger array of endodontic instruments. The drawings of the platform shows the usage of up to 10 such instruments; in practice, an endodontist may use up to 20 instruments on a single canal of a tooth. The drawings of this platform also show a medicament holder of a volume that is indicative of wastage of medicament.

Furthermore, this design is geared to be held by a single finger of the endodontist. Thus most of the work, e.g. determining the working length, choosing the correct instrument, etc., has to be done by the endodontist alone; a chairside assistant can help very little. The design is incompatible with teamwork and wastes the doctor's chair-time. Another drawback of the single finger-mounted design is the strain it imposes on the endodontist. The platform and the instruments it hold can be of sufficient weight that it becomes tiring and wearying for a carrier of such platforms in the course of a single endodontic procedure (one or more hours). Cross-contamination becomes a serious problem since the endodontist needs to record working length separately and contact other unsterilized material during the procedure. Cross-infection is also a serious issue in the case where a ruler is used and different cushions are deployed for different canals, at least one of which is infected. The infection spreads by use of the common ruler. Thus the hygienic state of the platform may be compromised in a number of ways.

U.S. Pat. No. 6,681,925 (Fischer et al.) is an autoclavable and resealable endo file container with an open ended including a body and a lid for closing the container. The lid is also configured for stabilizing the container in an upright position when the lid is placed over the bottom of the container. The lid is flared and generally provides greater support to the container for standing upright than does the bottom of the container. A foam material (e.g., open cell foam) housed within the container is used to hold dental instruments. A disinfecting solution contained within the container disinfects any dental instruments held therein.

The container disclosed in Fischer et al. has a number of disadvantages. It is designed to be re-used as in the case of the Kravitz platform; although it provides means for disinfecting instruments, the instrument must be placed in the foam material to receive the disinfectant.

SUMMARY OF THE INVENTION

This invention has an object to provide a single-use light weight platform for holding instruments during an endodontic procedure which is convenient for the professional and avoids cross-contamination and cross-infection, while allowing the safe and efficient collection of instruments after a procedure for cleaning purposes.

This invention provides for a platform for use with an instrument during an endodontic procedure comprising: a rigid pierceable body adapted for holding the instrument pierced partly therethrough; a linear measure disposed on a top surface of the body for determining length of an exposed segment of the instrument; and a reservoir on the top surface defined by the body for receiving a medicament.

In one aspect, the above linear measure comprises a scale; in a second aspect, the linear measure comprises a measure mound, the scale being placed along the axis of the measure mound. In another aspect, the linear measure comprises a longitudinal groove for aligning the instrument against the scale.

The platform may also include a removable marker for staking out distance along the linear measure having a sharpened edge or end point for piercing the linear measure.

The body or the measure mound may comprises a catch element for partially receiving a stopper of the instrument while establishing the working length of the instrument.

The platform may further include an attachment for mounting on fingers or a hand of a person.

A plurality of scoreable stage markings for indicating the stage of the endodontic procedure may also be part of the platform. The stage markings above may include MB, DB, ML, D, P, L, B, X and 4.

The reservoir may be defined by a top surface of the body and has a shape chosen from the group consisting of an open-ended trough, a cylinder, and a hemisphere.

The body of the platform may take the shape of a rectangular block.

The body may be constructed of a closed cell foam.

The body is preferably about 8 cm in length, 4 cm in depth, and 2.5 cm in height.

The platform may further comprise a bottom surface impenetrable to or resistant to penetration by the instrument.

The colour of the body may be primarily blue.

The platform may further comprise instruments pierced therein sufficient to complete the procedure on a single canal.

The instrument may be a file, a drill bit, and any other endodontic instrument.

The body may further comprise an instrument depot and an interchange depot on the top surface, and the interchange depot comprises a ready-for-use section and a used section.

The ready-for-use section may take the shape of a well for containing medicament.

This invention is also directed to a use of the platform described above for conducting an endodontic procedure on a single canal of a tooth.

Embodiments of this invention also includes a method of conducting an endodontic procedure on a canal of a tooth, comprising the steps of: (a) providing at an instrument depot of a platform with sufficient instruments for carrying out the procedure on a single canal, the platform comprising a rigid pierceable body adapted for holding the instrument pierced partly therethrough, a linear measure disposed on a top surface of the body for determining length of an exposed segment of the instrument and a reservoir on the top surface defined by the body for receiving a medicament; (b) providing a first person for assisting a second person to carry out the procedure, the first person holding the platform and partially cleaning used instruments; (c) retrieving an instrument from the interchange section by the second person; (d) using the instrument to carry out a part of the procedure; (e) returning the used instrument to the interchange depot; and (f) repeating above steps (c) to (e) until the procedure on the canal is completed.

DETAILED DESCRIPTION OF THE INVENTION

Figure 1:
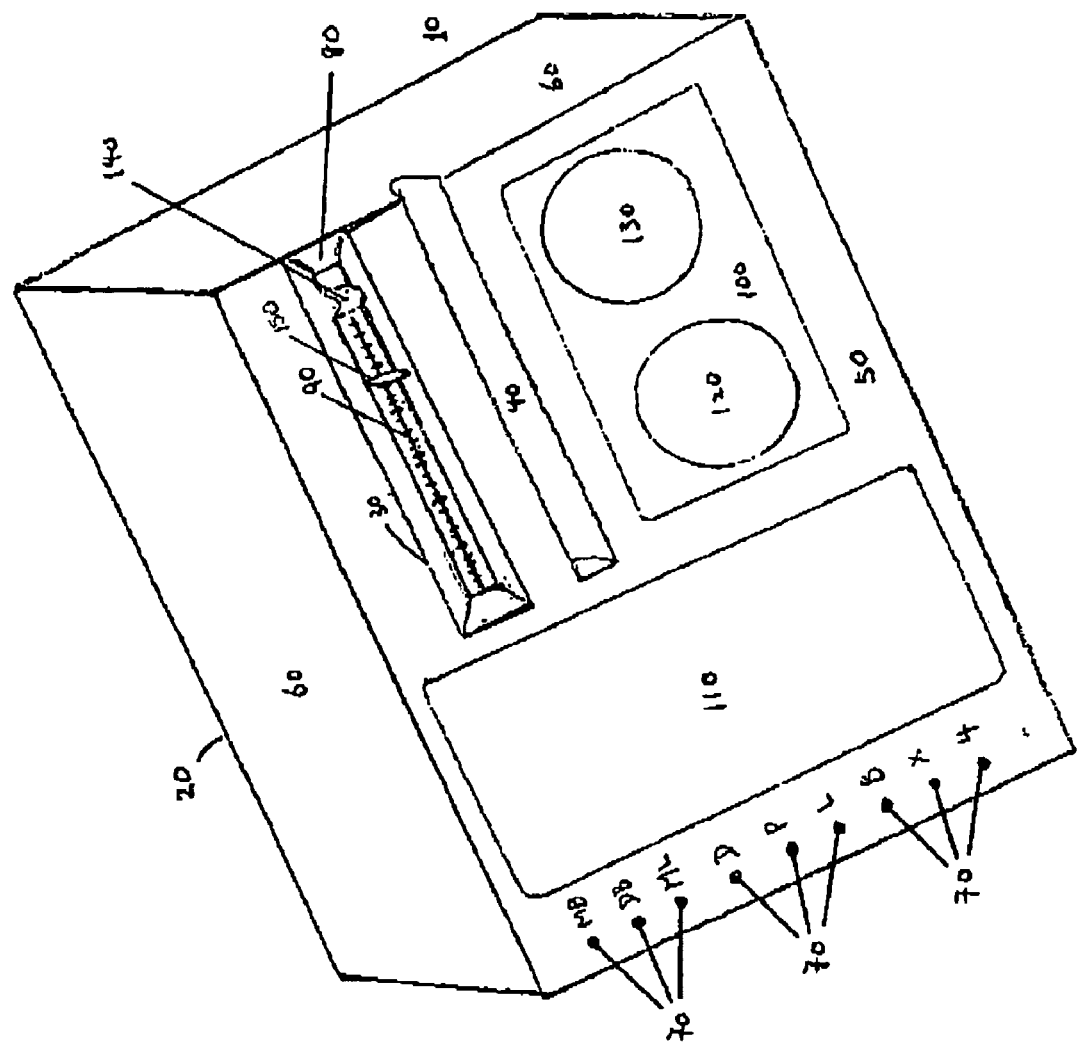
FIG. 1 is a perspective view of a preferred embodiment of the invention.

A detailed description of the embodiments of the invention will now be provided with specific reference to the drawing illustrating a preferred embodiment of the invention. Like structures will be provided with like reference numbers.

FIG. 1 is a perspective view of a preferred embodiment of the invention. The platform 10 comprises a body 20. The body 20 has a top surface 50, is rigid and generally pierceable, and typically made of a foam or foam-like material. The preferred material of the body 20 is a closed cell foam, such as STYROFOAM (also known as styrene foam or polystyrene plastic). This invention also includes open cell foams. The material further permits the dental professional (or his or her assistant) to handle or manipulate the platform 10 easily due to its light weight.

The general shape of the body 20 is preferably a substantially rectangular block with a relatively flat top surface 50 with considerably smaller height than its other linear dimensions (though not limited to such). The body 20 may be curved in a vertical cross-section, with an upward convexing top surface 50. Also contemplated is a block which has a horizontal cross-section the shape of two overlapping circles.

The dimensions of the body 20 is sufficiently large to hold dental instruments (with a sharp point such as a file or bit, or an edge) pierced on the body without becoming difficult to handle. Preferably the size of the body 20 is about 8 cm in length, 4 cm in depth, and 2.5 cm in height.

The shape of the platform 10 enables a large number of the platform 10 to be stored efficiently space-wise by close stacking.

Dental instruments (not shown) may be placed on the platform 10 since the body 20 is adapted to hold the instruments pierced partly therethrough. At least the top (and possibly all) surface 50 of the body 20 may be used to receive instruments. The material of the body 20 is chosen as indicated above to not cause any damage to the instruments during insertion or extraction from the body 20, nor to make it difficult for manual instrument insertion and extraction; yet it provides sufficiently strength to retain fast any inserted instrument therein and to provide one or more surfaces using which debris may be removed from an instrument by scraping the instrument against a surface or edge of the body 20 as a cleaning site.

Preferred embodiments of the platform 10 include a linear measure 30 on one exterior surface (preferably the top 50) of the body 20. The measure 30 preferably comprises a raised longitudinal measure mound 80. The linear measure 30 may be part of the body 20 (by some form of imprinting, marking, or engraving) or a separate piece affixed to the body 20. In the latter case, the linear measure 30 is also pierceable as the body 20.

The scale 90 of the measure 30 is typically marked in metric units of millimetres and centimetres, but other systems of linear measurement are also contemplated (e.g. English/Imperial). Numeric markings may also used along the scale 90. The measure 30 is intended to be used for deriving or controlling the length of exposed segments of dental instruments. A guide (not shown) in the form of a longitudinal groove may be part of the linear measure 30 (e.g. on top of or along the scale 90) to align an instrument for measurement against the scale 90.

Preferred embodiments include a removable marker (not shown) 150 having a narrow edge or sharpened end placed in the linear measure 30 (by piercing the surface using the narrow edge or sharpened end) at a point along the scale 90 (on the measure mound 80) to stake out the desired full working length, once such is determined. A dental assistant or professional may first determine the precise length of a working length of an instrument using the scale 90, and then place the marker at the correct spot on the measure 30. The working length may be established for any subsequent instrument for the canal by placing the stopper of the file against one edge of the block 20 and thrusting the instrument through the stopper along the scale 90 (e.g. groove) until the exposed file segment of the file matches the working length (i.e. the end of the file reaches the marker).

In a variation, either the body 20 or the raised mound 80 may define a catch element 140 at one end of the scale 90 for trapping and keeping the stopper from moving while the instrument is thrusted through the stopper along the scale 90 (e.g. groove) until the exposed segment of the instrument matches the desired working length. This catch element 140 is preferably a space in the shape of a semi-disk of sufficient thickness and radius to trap a stopper inserted therein keeping it from moving in any direction parallel to the scale 90.

A single platform 10 may have more than one linear measure 30 on different areas of the platform 10. For example in the case of a rectangular block platform 10, a linear measure 30 may be on two or more rectangular surfaces of the platform 10 for ease of use, or be placed on opposing side of the top surface 50 to permit both left and right-handed usage.

The body 20 should allow markings to be readily made thereon using a dental instrument by indentation visible to the eye. For example, one file or drill bit may be used to make a marking as to the working length (instead of the marker).

These features remove the risks posed by cross contamination between the instruments and any external implement for marking a length along a measure (such as a pencil or marker). In the prior art, the length is recorded by such an implement.

The platform 20 includes an indication of the particular stage of a procedure. A preferred embodiment includes stage markings 70 on the top surface 50. For example, each nerve (typically one of a maximum of four in a tooth) may constitute one stage for a root canal. The preferred number of stage markings 70 is 9 and the preferred stage markings 70 are MB, DB, ML, D, P, L, B, 4 and X (no particular order), the meanings of which are clear to a dental professional, arranged in a linear fashion. X may be used as a catch-all marking. Another simpler preferred set of stage markings 70 comprises numerical stage markings 70, e.g. 1, 2, 3, and 4. Each time a new stage commences, the professional or assistant preferably retrieves a new platform 20, and using the stage marking 70 corresponding to the stage, keeps track of the stage. For example, the assistant may use a drill bit to score the stage marking 70 MB corresponding to the stage for working on the meso-buccal nerve on commencing work on that nerve. As a result, this removes the possibility of using a file on one nerve with an incorrect working length intended for another canal.

The stage markings 70 may be part of the body 20 (by some form of imprinting or marking) or a separate affixed piece. The stage markings 70 are positioned preferably in a linear sequential fashion along one top edge of the body 20 so as to facilitate the scoring thereof.

The indication of the particular stage of a procedure may instead be a colour, whether being part of, or the entirety of the body 20.

A reservoir 40 for medicament used during the ondodontic procedure, such as a sterilizing fluid, is defined by the body 20 on one or more surfaces of the body 20. Preferably the medicament reservoir 40 is defined on the top surface 50 of the body 20. It may also be on a side surface 60, which is particularly useful where the medicament is highly viscous.

The particular shape of the reservoir 40 may be varied. The preferred shapes for a reservoir 40 defined by the top surface 50 are a trough with one end open at a side surface of the body (thereby permitting application of the fluid to the entire working length of a file), and a cylindrical or a semi-spherical well.

The body 20 may have a bottom surface (not shown) coated or plated with a material such as to render that the bottom surface impenetrable to or resistant to penetration by an instrument. This way, a person holding the platform 10 over his or her palm (supported either by fingers or the palm) is protected against accidental injury by prickling with an instrument inserted from the top surface 50.

The platform 10 may be adapted to be attached to a physical part of a dental professional or his/her assistant during an ondodontic procedure. For example, the platform 10 may be shaped to be comfortably held by the fingers or palm of one hand (e.g. contours or guides to fit fingers); or have attachments to be secured to one or more fingers, wrist, or even arm of a person. An adapter (not shown), for example, an open or closed ring, with a possible flat support surface, may be used to secure the platform 10 to a finger of the user (the adapter being either integral to the platform 10 or attached thereto by, for example, one or more spikes being part of the adapter).

Since almost all sides of the body 20 may be used to retain instruments, the user may manipulate with one hand the platform 10 such to have the platform 10 in any position in terms of yaw, pitch and roll. This can be of particular use in the course of a longer procedure where substantial debris may be generated on the instruments and it is preferred to remove such debris in different cleaning sites of the block 20 at various points of the procedure.

The platform 10 as a whole is preferably single-use and disposable after carrying out a procedure on a single canal of a tooth. Packaging may be used to contain the platform(s) 10 prior to an endodontic procedure for preservation of its hygienic and sanitary state and subsequently for safe disposal. A dental assistant may remove a platform 10 from its packaging, insert the requisite files (and possibly drill bits), all in time for the ondodontic procedure to commence. The assistant may also handle the platform 10 during the procedure to ease the burden on the professional, including possibly placement of the instruments. An assistant would require little, if any, training to take a significant burden off the dental professional. In a variation of the above embodiments, the top surface 50 defines two regions: an interchange depot 100 and an instrument depot 110. The endodontic instruments (typically colour coded for files) are typically placed at the instrument depot 110. The interchange depot 100 has 2 sections: a ready-for-use section 120 and a used section 130. When an instrument is next to be used in a procedure, the assistant would transfer the instrument from the storage depot 110 to the ready-for-use section 120 (whether under specific instructions from the professional or following fairly standard guidelines); the dental professional places a just-used instrument in the used section 130 for subsequent processing by the assistant typically to clean the instrument and relocation to the storage depot 110. In this fashion, the dental professional can focus on the procedure and less on the instrument or instructing the assistant.

These regions 100 110 and sections 120 130 may be areas on the top surface 50 demarcated as such by marking or colour. The ready-for-use section 120 may also take the form of a shallow well for containing medicament so as to relieve the professional from having to add medicament from the reservoir 40 to an instrument placed in the ready-for-use section 120 before using the instrument.

Alternatively, the professional may perform the procedure and handle the platform 10 independently of the assistant without need for the interchange depot 100 or the instrument depot 110.

The colour of the body 20 and various elements on the body 20 may be various and not limited; keeping in mind the use of colour as the indication of the particular stage of a procedure, the preferred colours for the body 20 are nonetheless blue or any non-white colour. The stage markings 70 (when present) and linear measure 30 should be in a colour which provides sufficient contrast to the colour of the body 20.

The invention thus presented has further benefits. Typically after a procedure an assistant will deposit instruments into a container for an initial water rinsing and washing of the accumulated debris. Endodontic instruments are small, fragile and usually sharp. An assistant concerned about personal safety may prefer to dump instruments (not using the platform 10 of the present invention) in the container resulting in compromises to the integrity of some instruments. This may lead to later breakage of the instrument while inserted in a canal, recovery of which is very difficult. Embodiments of the present invention bearing the inserted instruments may be tossed in their entirety in a water bath without causing damage to the said instruments. Since the preferred construction of the body 20 is foam, the platform 10 will float, making the later retrieval of the instruments easy. The assistant may then use various sites on the body 20 for scraping off debris during rinsing of the instruments and prior to ultrasonic and autoclave cleaning. The platform 10 may then be disposed of.

It will be appreciated that the above description relates to the preferred embodiments by way of example only. Many variations on the system and method for delivering the invention will be clear to those knowledgeable in the field, and such variations are within the scope of the invention as described and claimed, whether or not expressly described.

What is claimed is:

1. A platform for use with an instrument during an endodontic procedure comprising:
    a rigid pierceable body adapted for holding the instrument pierced partly therethrough;
    a linear measure disposed on a top surface of the body for determining length of an exposed segment of the instrument; and
    a reservoir on the top surface defined by the body for receiving a medicament.

2. The platform of claim 1, wherein the linear measure comprises a scale.

3. The platform of claim 2, wherein the linear measure comprises a measure mound, the scale being placed along the axis of the measure mound.

4. The platform of claim 2, wherein the linear measure comprises a longitudinal groove for aligning the instrument against the scale.

5. The platform of claim 1, further comprising a removable marker for staking out distance along the linear measure having a sharpened edge or end point for piercing the linear measure.

6. The platform of claim 3, wherein the body or the measure mound comprises a catch element for partially receiving a stopper of the instrument while establishing the working length of the instrument.

7. The platform of claim 1, further comprising an attachment for mounting on fingers or a hand of a person.

8. The platform of claim 1, further comprising a plurality of scoreable stage markings for indicating the stage of the endodontic procedure.

9. The platform of claim 8, wherein the stage markings are MB, DB, ML, D, P, L, B, X and 4.

10. The platform of claim 1, wherein the reservoir is defined by a top surface of the body and has a shape chosen from the group consisting of an open-ended trough, a cylinder, and a hemisphere.

11. The platform of claim 1, wherein the body has the shape of a rectangular block.

12. The platform of claim 1, wherein the body is constructed of a closed cell foam.

13. The platform of claim 1, wherein the body is about 8 cm in length, 4 cm in depth, and 2.5 cm in height.

14. The platform of claim 1, wherein the platform comprises a bottom surface impenetrable to or resistant to penetration by the instrument.

15. The platform of claim 1, further comprising instruments pierced therein sufficient to complete the procedure on a single canal of a tooth.

16. The platform of claim 1, wherein the instrument is chosen from the group consisting of a file and a drill bit.

17. The platform of claim 1, wherein the body further comprises an instrument depot and an interchange depot on the top surface, and the interchange depot comprises a ready-for-use section and a used section.

18. The platform of claim 17, wherein the ready-for-use section is a well for containing medicament.

19. A method of conducting an endodontic procedure on a single canal of a tooth, using the platform of claim 17, comprising the steps of:
    (a) providing the instrument depot of the platform with sufficient instruments for carrying out the procedure on the single canal of a tooth;
    (b) providing a first person for assisting a second person to carry out the procedure, the first person holding the platform and partially cleaning used instruments;
    (c) retrieving and instrument from the interchange depot by the second person;
    (d) using the instrument to carry out a part of the procedure;
    (e) returning the used instrument to the interchange depot; and
    (f) repeating steps (c) to (e) until the procedure on the single canal of a tooth is completed.

* * * * *